United States Patent [19]

Kurobe et al.

[11] Patent Number: 5,166,328
[45] Date of Patent: Nov. 24, 1992

[54] S-ADENOSYLMETHIONINE DERIVATIVES

[75] Inventors: Hiroshi Kurobe; Tomokazu Sugawara; Takeshi Endo, all of Toyama, Japan

[73] Assignee: Fuji Kagaku Kogyo Kabushiki Kaisha, Toyama, Japan

[21] Appl. No.: 623,646

[22] PCT Filed: Apr. 27, 1990

[86] PCT No.: PCT/JP90/00555
§ 371 Date: Dec. 21, 1990
§ 102(e) Date: Dec. 21, 1990

[87] PCT Pub. No.: WO90/13557
PCT Pub. Date: Nov. 15, 1990

[30] Foreign Application Priority Data

Apr. 28, 1989 [JP] Japan .................................. 1-110946

[51] Int. Cl.$^5$ ............................................ C07H 19/167
[52] U.S. Cl. ............................................ 536/26; 536/24
[58] Field of Search .............................. 536/26; 514/46

[56]  References Cited

U.S. PATENT DOCUMENTS

| | | | |
|---|---|---|---|
| 3,954,726 | 5/1976 | Fiecchi | 536/26 |
| 4,028,183 | 6/1977 | Fiecchi | 536/26 |
| 4,057,686 | 11/1977 | Fiecchi | 536/26 |
| 4,373,097 | 2/1983 | Stramentinoli et al. | 536/26 |
| 4,454,122 | 6/1984 | Stramentinoli et al. | 514/46 |
| 4,465,672 | 8/1984 | Gennari | 514/46 |
| 4,558,122 | 12/1985 | Gennari | 536/26 |
| 4,764,603 | 8/1988 | Zappia et al. | 536/26 |

FOREIGN PATENT DOCUMENTS 0074555  3/1983  European Pat. Off. .
2217706A 1/1989  United Kingdom .

OTHER PUBLICATIONS

Chemical Abstract; vol. 95; No. 3; Abstract No. 18222v; "S-adenosylmethionine excites rat cerebral cortical neurons"; p. 54; J. W. Phillis; Jul. 20, 1981.

Chemical Abstracts; vol. 108; No. 7; Abstract No. 49255z; p. 68; "S-adenosyl-L-methionine prevents ischemic neuronal death"; Y. Matsui et al., Feb. 15, 1988.

*Primary Examiner*—Johnnie R. Brown
*Assistant Examiner*—L. E. Crane
*Attorney, Agent, or Firm*—Birch, Stewart, Kolasch & Birch

[57]  ABSTRACT

Novel S-adenosylmethionine derivatives useful as medicament are provided which are represented by the following general formula (I):

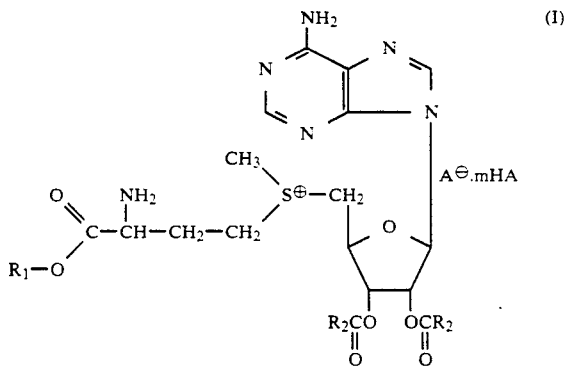

wherein $R_1$ and $R_2$ each represent straight or branch alkyl or alkenyl having 1-10 carbon atoms; m is 1-3; and A is an anion of inorganic or organic acids.

4 Claims, No Drawings

S-ADENOSYLMETHIONINE DERIVATIVES

DESCRIPTION

1. Technical Field

This invention relates to novel S-adenosylmethionine derivatives, which are high in fat-solubility and yet can, when used as medicament, readily release S-adenosylmethionine in the living body.

2. Background Art

S-adenosylmethionine (SAM) is known as a substance existing in the living body and also as a methyl donor in the metabolism of living organisms.

As pharmacological action of SAM, various actions such as prolongation of life of mouse under hypoxia, improvement of energy state of ischemic brain, improvement of cerebral energy metabolism and acidosis of the model with recirculated blood flow following ischemia, etc. have been heretofore found.

SAM is also known to show a variety of actions, i.e. inhibition of neuronal death following ischemia, improvement of cerebral glucose utility, inhibition of brain edema, improvement of EEG, improvement of evoked potential, ameliorative action on motor function, and therefore reported to be important as a cure for stroke. SAM, however, possesses water-soluble groups such as hydroxyl group, amino group, sulfonium group, carboxyl group, etc. in its molecule, therefore being poor in permeability through cell barrier and causing a problem in drug absorption when orally administered.

In order to render SAM orally applicable, the development of a SAM derivative, which 1) has a good permeability through cell barrier and 2) can release SAM promptly after permeation is desired.

As compounds satisfying requirement 1) above, (a) a compound obtainable by esterifying the carboxylic acid and the 2'- and 3'- hydroxyl groups while simultaneously acylating the amino group of SAM, (b) a compound obtainable by esterifying the 2'- and 3'- hydroxyl groups while simultaneously acylating the amino group of SAM, etc. have already been reported (Japanese Unexamined Patent Application Publication No. 57397/83 (TOKKAI-SHO 58-57397)). These derivatives, however, show poor susceptibility of hydrolysis in the living body as they contain amide bonds, and do not adequately fulfil requirement 2), i.e. prompt release of SAM after permeation through cell barrier. Accordingly, the development of a novel SAM derivative that can satisfy both requirements 1) and 2) above concurrently has been desired.

DISCLOSURE OF INVENTION

The object of this invention is to provide substances which are high in fat-solubility and are easy to permeate through cell barrier and yet can readily release SAM in the living body.

The present inventors have found that novel SAM derivatives represented by formula (I) below, i.e. acid-addition salts of compounds obtained by esterifying the hydroxyl groups only among the above-mentioned water-soluble groups of SAM, are high in fat-solubility, easily permeate through cell barrier and are capable of easily releasing SAM in the living body.

Accordingly, this invention provides novel SAM derivatives of the following formula (I)

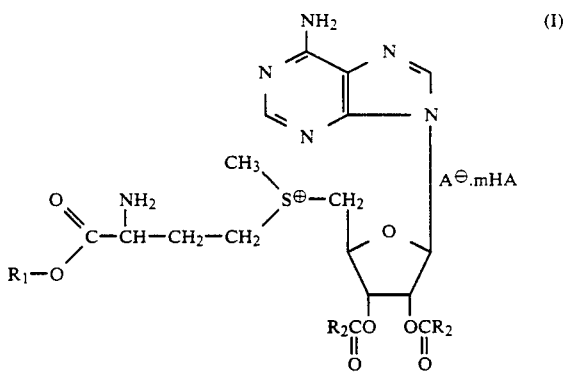

wherein $R_1$ and $R_2$ each represent straight or branched alkyl or alkenyl having 1–10 carbon atoms; m is 1–3; and A is an anion of inorganic or organic acids.

In the above-mentioned formula (I), examples of $R_1$ and $R_2$ include: for straight alkyl, methyl, ethyl, propyl, butyl and decyl; for branched alkyl, isopropyl and tert-.butyl; and, for alkenyl, decenyl. Furthermore, m stands for 1–3 and A for an anion of inorganic or organic acids.

Examples of the derivatives of the above-mentioned formula to which to add an inorganic or organic acid include:

Compound A: 2',3'-O-dibutanoyl-S-adenosylmethionine methyl ester, and

Compound B: 2',3'-O-didecanoyl-S-adenosylmethionine methyl ester.

Examples of HA in the above-mentioned formula (I) include, for inorganic acid, hydrochloric, hydrobromic, sulfuric and phosphoric acids and, for organic acid, organic sulfonic acids such as methane-, ethane-, benzene- and p-toluenesulfonic acids and carboxylic acids such as citric, tartaric and succinic acids. Preferred examples are inorganic acids and organic sulfonic acids.

One of the most preferred examples of $A^-$ is $CH_3SO_4^-$.

The S-adenosylmethionine derivatives of the above-mentioned formula (I) are hereinafter referred to as "Acid-addition salt (I)".

Acid-addition salt (I) of the present invention can be prepared by the following method.

S-adenosyl-L-homocysteine (SAH) (II) of the formula (II) below and trichloroethyloxycarbonyl chloride, both used as starting material, are first brought into reaction to give Compound (III) of the formula (III) below.

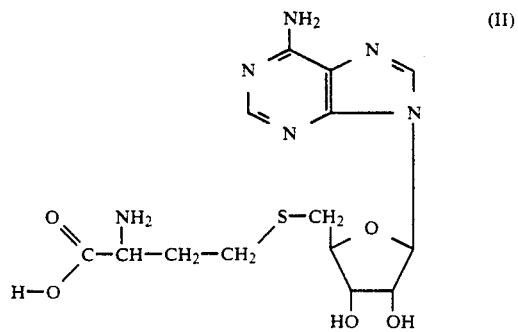

-continued

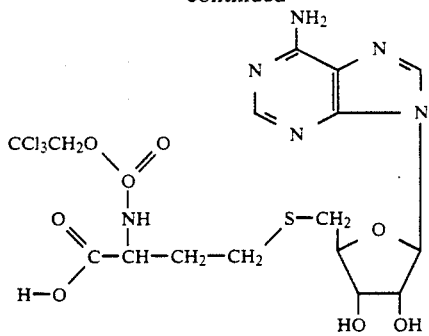

The compound of the formula (III) above is reacted in the presence of thionyl chloride with an alcohol of the following formula (IV)

  $R_1-OH$ (IV)

wherein $R_1$ represents straight or branched alkyl or alkenyl having 1-10 carbon atoms, to give an esterified compound of the following formula (V)

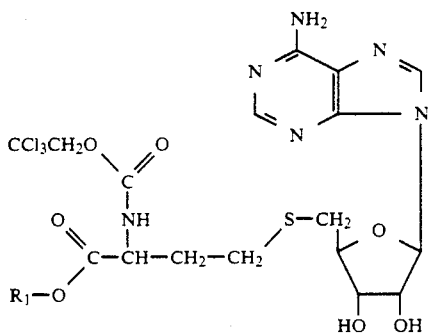

The esterified compound of the formula (V) above is reacted in the presence of a base such as triethylamine with a reactive derivative, e.g. halide or anhydride, of a fatty acid of the following formula (VI)

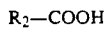  $R_2-COOH$ (VI)

wherein $R_2$ represents straight or branched alkyl or alkenyl having 1-10 carbon atoms, to give a compound of the following formula (VII)

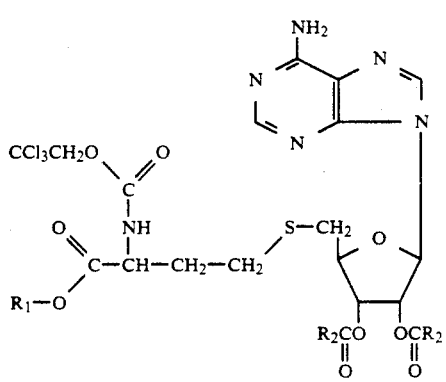

The protective group, i.e. the trichloroethyloxy carbonyl group, attached to the NH group of the compound of the formula (VII) above is then removed in an aqueous acetic acid solution using zinc powder to give a compound of the following formula (VIII)

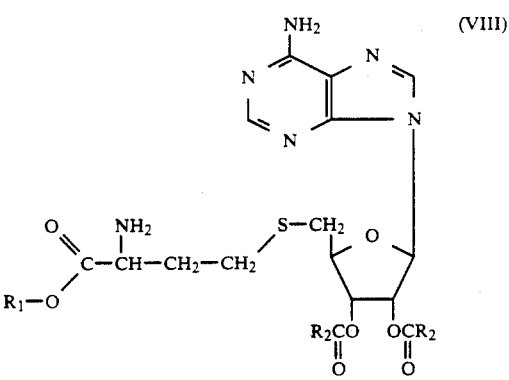

The compound of the formula (VIII) above is treated with a methylating agent such as dimethyl sulfate or methyl iodide to methylate the S atom.

In the foregoing description, the introduction of a protective group into the amino group of SAH is carried out, by the way of example, by reaction of trichloroethyloxycarbonyl chloride with SAH. It being understood, however, that such introduction of a protective group into the amino group may be achieved by using any customary protective group for the protection of amino groups as well as any method ordinarily used for the introduction, of such protective groups into amino groups.

Various operational means may be applied to each of the above-mentioned reaction steps which are conventionally used for the respective reactions.

The acid-addition salt (I) of the present invention is useful as a remedy for ischemic brain diseases.

The utility of Acid-addition salt (I) as a remedy for ischemic brain diseases is shown by the fact that it is very effective for the prevention of the death of cerebral hippocampal cells when administered intravenously or orally to experimental animals 30 or 60 minutes prior to cerebral ischemia.

In the case of oral administration, Acid-addition salt (I) is by far more effective than SAM, and is therefore particularly useful for oral administration.

Furthermore, Acid-addition salt (I) shows similar pharmacological effects to those of SAM mentioned above.

Acid-addition salt (I) can be administered in any form orally or parenterally. For instance, it can be administered in tablet, capsule or other dosage forms. Furthermore such dosage forms may be prepared by using carriers customary in drug preparation.

The pharmacological test made with Acid-addition salt (I) and the results thereof are described in detail in the following.

EXPERIMENTAL EXAMPLE 1

Inhibitory effect against death of hippocampal neurons by intravenous administration The vertebral artery beneath the first cervical vertebra of male Wister rats (240-270 g) was coagulated with an electrocautery, and on the following day the test compound (acid-addition salt of Compound A) was dissolved in physiological saline to give, after pH adjustment to 5 with phosphate buffer, a 1.54 mg/ml solution. This solution was intravenously administered (7.7 mg/kg). Thirty minutes after that bilateral common carotid arteries were occluded with clips to induce forebrain ischemia for 10 minutes.

Seven days thereafter the brain was removed and a microscopic specimen of its hippocampal region was prepared and the number of neurons per 1 mm of hippocampal CA1 pyramidal cell layer was measured.

To the control group physiological saline was administered (0.5 ml/100 g) intravenously at the start of recirculation.

SAM trihydrochloride used for comparison was dissolved in physiological saline, and the solution was adjusted to pH 6 with an acqueous sodium phosphate solution and administered (100 mg/kg) intravenously at the start of recirculation.

The U test was used for statistical analysis.

EXPERIMENTAL EXAMPLE 2

Inhibitory effect against death of hippocampal neurons by oral administration

Rats were used to which the same treatment had been applied as was carried out prior to the administration of test compound in Experimental example 1. Test compound (acid-addition salt of Compound B) was dissolved in physiological saline as described for Compound A in Experimental example 1 to prepare a 10 mg/ml solution. This solution was orally administered (50 mg/kg) 60 minutes before ischemia. To the control group physiological saline was orally administered (0.5 ml/100 g).

SAM trihydrochloride used for comparison was dissolved in physiological saline and the solution was then adjusted to pH 6 and was administered (400 mg/kg) orally at the start of recirculation.

Results

The results of these tests are shown in Tables 1 and 2. As can be seen from these tables, in the group to which the acid-addition salt of 2′,3′-O-dibutanoyl-S-adenosylmethionine methyl ester (Compound A) was intravenously administered (7.7 mg/kg) 30 minutes prior to ischemia, the number of surviving neurons was $128\pm52.0$ and in the group to which the acid-addition salt of 2′,3′-O-didecanoyl-S-adenosylmethionine methyl ester (Compound B) was orally administered (50 mg/kg), the number of surviving neurons was $148\pm48.6$, thus each showing a significant effect as compared with the corresponding control group.

TABLE 1

Effect of SAM derivative on inhibition of death of hippocampal neurons (intravenous administration)

| Test compound | Dose (mg/kg) | Number of surviving neurons (per mm) |
| --- | --- | --- |
| Control | — | 77 ± 34.8 |
| Acid-addition salt of Compound A | 7.7 | 128 ± 52.0* |
| SAM trihydrochloride | 100 | 111 ± 60.1 |

*$P < 0.05$: physiological saline is used as control

TABLE 2

Effect of SAM derivative on inhibition of death of hippocampal neurons (oral administration)

| Test compound | Dose (mg/kg) | Number of surviving neurons (per mm) |
| --- | --- | --- |
| Control | — | 77 ± 34.8 |
| Acid-addition salt of Compound B | 50 | 148 ± 48.6** |

TABLE 2-continued

Effect of SAM derivative on inhibition of death of hippocampal neurons (oral administration)

| Test compound | Dose (mg/kg) | Number of surviving neurons (per mm) |
| --- | --- | --- |
| SAM trihydrochloride | 400 | 90 ± 31.4 |

**$P < 0.01$: physiological saline is used as control

In the following are given some examples of preparation of Acid-addition salt (I) according to the present invention.

EXAMPLE 1

Process of preparation of acid-addition salt of 2′,3′-O-didecanoyl-S-adenosylmethionine methyl ester (Compound B)

(a) To a solution of 17.3 g of S-adenoyl-L-homocysteine (SAH) and 13.8 g of potassium bicarbonate in 250 ml of water was added dropwise a solution of 14 g of trichloroethyloxycarbonyl chloride in 40 ml of ether under ice cooling. After stirring for 4 hours at room temperature, the reaction mixture was washed with chloroform (100 ml × 3 times), filtered to remove insolubles and adjusted to pH 3 with concentrated hydrochloric acid. Precipitated crystals were separated by filtration to obtain 21.8 g of N-(trichloroethyloxycarbonyl)-SAH.

NMR (CD$_3$OD)δ: 1.75–2.30(2H, m), 2.50–2.80(2H, m), 2.8–3.1(2H, m), 4.1–4.5(3H, m), 4.75(1H, d(J=12.4Hz)), 4.77(1H, d(J=12.4Hz)), 6.00(1H, d(J=4.88Hz)), 8.21(1H, s), 8.30(1H, s).

(b) To a solution of 20 g of the above-mentioned N-(trichloroethyloxycarbonyl)SAH in 1 l of methanol was added dropwise 8.5 g of thionyl chloride under cooling (minus 15° C.). The reaction mixture was condensed under reduced pressure and neutralized with sodium bicarbonate. Inorganics were filtered off and the solvent was distilled off. Then the residue was purified by column chromatography using silica gel (chloroform:methanol=95:5) to obtain 17.3 g of N-(trichloroethyloxycarbonyl)SAH methyl ester.

NMR (CD$_3$OD)δ: 1.8–2.15(2H, m), 2.5–2.75(2H, m), 2.8–3.05(2H, m), 3.68(3H, s), 4.05–4.5(3H, m), 4.77(2H, s), 6.00(1H, d(J=4.88Hz)), 8.21(1H, s), 8.30(1H, s).

(c) To a solution of 15 g of the above-mentioned ester and 6.2 g of triethylamine in 200 ml of acetonitrile was added 18 g of decanoic anhydride and the mixture was stirred for 18 hours at room temperature. After distilling off the solvent, the residue was purified by column chromatography using silica gel (chloroform:methanol=99:1) to obtain 17.7 g of N-(trichloroethyloxycarbonyl)-2′,3′-O-didecanoyl-SAH methyl ester.

NMR (CD$_3$OD)δ: 0.88(6H, t), 1.0–1.8(28H, m), 1.8–2.75(8H, m), 2.85–3.1(2H, m), 3.78(3H, s), 4.25–4.6(2H, m), 4.72(1H, d(J=12.4Hz)), 4.74(1H, d(J=12.4Hz)), 5.59(1H, dd), 5.91(1H, t), 6.15(1H, d(J=5.4Hz)), 8.10(1H, s), 8.09(1H, s), 8.29(1H, s).

(d) 17.7 g of N-(trichloroethyloxycarbonyl)-2′,3′-O-didecanoyl-SAH methyl ester was dissolved in 220 ml of an aqueous acetic acid solution (acetic acid/water=10:1), and after adding 42 g of zinc powder the mixture was stirred for 10 hours at room temperature. Insolubles were filtered off and the solvent was distilled off. The residue was dissolved in ethyl acetate and the solution was neutralized with an aqueous sodium bicarbonate solution. The organic layer was washed with water and dried (anhydrous sodium sulfate). The solvent was distilled off and the residue was purified by column chromatography using silica gel (Chloroform/methanol=98:2) to obtain 10.7 g of 2',3'-O-didecanoyl-SAH methyl ester.

NMR (CD$_3$OD)δ: 0.82(6H, t), 1.1-3.15(38H, m), 3.53(dd), 3.67(3H, s), 4.25-4.50(1H, m), 5.66(1H, dd(J=4.39Hz, 5.61Hz)), 6.05(1H, t(J=5.61Hz)), 6.21(1H, d(J=5.61Hz)), 8.23(1H, s), 8.31(1H, s).

(e) To a solution of 10.7 g of the above-mentioned 2',3'-O-didecanoyl-SAH methyl ester in 230 ml of a mixture of formic acid and acetic acid (1:1) was added dropwise 5.1 g of dimethyl sulfate under ice cooling. After stirring for 8 days at room temperature, the solvent was distilled off and ether was added to the residue to precipitate a white solid. This solid was separated by filtration, washed with ether and dried to obtain 10.2 g of acid-addition salt of Compound B as white powdery solid.

NMR (CD$_3$OD)δ: 0.89(6H, t), 1.1-1.85(28H, m), 2.2-2.6(6H, m), 3.04, 3.01(3H, brs), 3.69(9H, s), 3.82, 3.86(3H, s, s), 4.00-4.40(3H, m), 5.70-6.05(2H, m), 6.40(1H, d(J=3.66Hz)), 8.50(1H, s), 8.54(1H, s).

EXAMPLE 2

Process of preparation of acid-addition salt of 2',3'-dibutanoyl-S-adenosylmethionine methyl ester (Compound A)

Acid-addition salt of Compound A was obtained by carrying out the process in the same manner as described in Example 1 except that butanoic anhydride was used instead of decanoic anhydride used in Example 1 (c).

NMR (CD$_3$OD)δ: 0.92(3H, t(J=6.83Hz)), 0.99(3H, t(J=6.84Hz)), 1.4-1.85(2H, m), 2.2-2.6(6H, m), 3.00, 3.03(3H, s, s), 3.69(9H, s), 3.82, 3.86(3H, s, s), 3.95-4.30(3H, m), 5.70-6.05(2H, m), 6.38(1H, d(J=3.66Hz)), 8.46(1H, s), 8.50(1H, s).

We claim:

1. A S-adenosylmethionine derivative of the general formula (I)

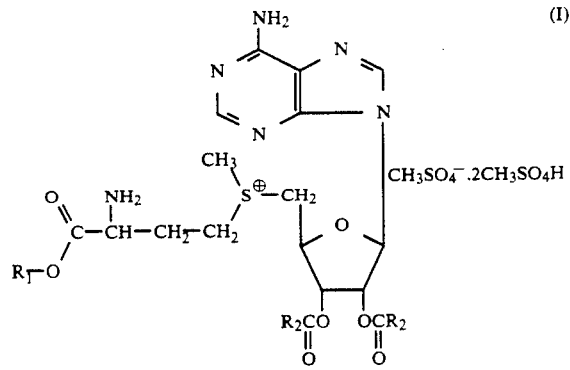

wherein R$_1$ and R$_2$ each represent straight or branched alkyl having 1-10 carbon atoms.

2. The S-adenosylmethionine derivative as claimed in claim 1 wherein the derivative of the general formula (I) is a methyl sulfate ion-methyl sulfuric acid addition salt of 2',3'-O-dibutanoyl-S-adenosylmethionine methyl ester.

3. The S-adenosylmethionine derivative as claimed in claim 1 wherein the derivative of the general formula (I) is a methyl sulfate ion-methyl sulfuric acid addition salt of 2',3'-O-didecanoyl-S-adenosylmethionine methyl ester.

4. The S-adenosylmethionine derivative as claimed in claim 1, wherein R$_1$ and R$_2$ are selected from the group consisting of methyl, ethyl, propyl, butyl, decyl, isopropyl, and tertiary butyl.

* * * * *